United States Patent [19]
Fujimoto et al.

[11] 3,936,469
[45] Feb. 3, 1976

[54] PROCESS FOR PREPARING N-CARBOXYLIC ANHYDRIDES OF AMINO ACIDS

[75] Inventors: Yasuo Fujimoto, Yokohama; Keizo Tatsukawa, Machida; Yoichi Koiwa, Tokyo; Akira Miike, Machida; Tatsuo Nomura, Tokyo; Shohei Kobayashi, Kooriyama, all of Japan

[73] Assignee: Kyowa Hakko Kogyo Kabushiki Kaisha, Tokyo, Japan

[22] Filed: Nov. 12, 1973

[21] Appl. No.: 415,016

[30] Foreign Application Priority Data
Nov. 13, 1972 Japan................ 47-112891
Jan. 31, 1973 Japan................ 48-11924

[52] U.S. Cl.............................. 260/307 B
[51] Int. Cl.² ........................... C07D 263/44
[58] Field of Search ................. 260/307 B

[56] References Cited
UNITED STATES PATENTS
2,406,186   8/1946   Baldwin et al. ............ 260/561
3,822,281   7/1974   Fujimoto et al. .......... 260/307 B FOREIGN PATENTS OR APPLICATIONS
3,091   12/1963   Japan Primary Examiner—Raymond V. Rush
Attorney, Agent, or Firm—Phillips, Moore, Weissenberger, Lempio & Strabala

[57] ABSTRACT

This invention relates to an improved process for preparing N-carboxylic anhydrides of amino acids, and N-carboxylic anhydrides of derivatives of amino acids by reacting an amino acid, a derivative of amino acid or a salt thereof with trichloromethylchloroformate in an organic solvent, preferably a mixture of an ether or ester with one or more other organic solvents and adding to the reaction mixture carbon, basic aluminum chloride or aluminum oxide just before or immediately after completion of the initial reaction.

5 Claims, No Drawings

PROCESS FOR PREPARING N-CARBOXYLIC ANHYDRIDES OF AMINO ACIDS

BACKGROUND AND BRIEF SUMMARY OF THE INVENTION

In this specification, the term "amino acids" denotes amino acids and their derivatives; while "N-carboxylic anhydrides" and "N-carboxylic anhydrides of amino acids" are referred to as "NCA" and "ANCA", respectively; and "trichloromethylchloroformate", i.e., ($CCl_3OCOCl$) is referred to as "TCF".

It is known to prepare ANCA by suspending an amino acid or its salt in an organic solvent, reacting the suspension with phosgene blown thereinto at an elevated temperature of about from 40° to 100°C and cooling the reaction mixture to effect crystallization of the ANCA. However, the use of phosgene, which is poisonous gas is quite dangerous. Furthermore, because the boiling point of phosgene is 8.2°C (measured at 760 mmHg), there is a great probability that phosgene blown into the reaction system is liable to escape therefrom.

The reaction for preparing ANCA from amino acid and phosgene is considered to proceed in the following manner:

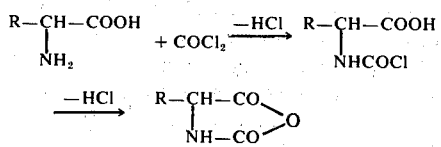

wherein R is an amino acid radical. [Advance in Protein Chemistry, Vol. 3, page 268 (1958), Academic Press Inc. Publisher, New York, N.Y.]

In these series of reactions, the latter reaction proceeds faster than the former, i.e., one third of the amino acid in the starting mixture is quickly converted into ANCA; while the remaining two thirds of the amino acid is considered to be readily converted into the hydrochloride thereof represented by

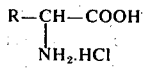

by the action of the by-product hydrogen chloride. The reaction for obtaining ANCA from amino acid and phosgene proceeds with a high velocity, while the velocity of the reaction between the hydrochloride of amino acid and phosgene is relatively slow. The reaction velocity of dehydrogenchloride to give NCA is accelerated by elevating the reaction temperature. However, when the temperature of the reaction system is elevated, the concentration of the phosgene dissolved in the reaction solvent reduces, resulting in slow reaction velocity to NCA. It is necessary for acceleration of the reaction velocity to dissolve a largest possible amount of phosgene in the solvent at an elevated reaction temperature. However, the use of a large amount of solvent for this purpose is very disadvantageous in industrial practice; and even if such a large amount of solvent is used, it is usually necessary to use more than 2–3 mols of phosgene per mol of the amino acid or its salt, utilized in the reaction.

In order to increase the solubility of phosgene in the solvent and/or to accelerate the reaction valocity, various attempts such as acceleration of agitation and improvement of gas-charging devices, etc. have been made. However, because of the very corrosive nature of both phosgene and hydrogen chloride which is given off during the reaction, it is difficult to achieve the desired purposes.

It has now unexpectedly been discovered that the reaction for preparing ANCA from amino acids can be carried out by using TCF in place of phosgene, which is a health hazard.

It is therefore an object of the present invention to provide a process for preparing ANCA from amino acids and salts thereof in a simple manner and without any deleterious influence upon human health.

Another object of the present invention is to provide a process for preparing ANCA having a higher quality.

It is another object of the invention to provide a process for preparing ANCA by reaction of amino acids with TCF.

DETAILED DESCRIPTION OF THE INVENTION

According to the present invention, there is provided a process for preparing ANCA from amino acids and salts thereof, wherein an amino acid is suspended in an organic solvent and TCF is dissolved to said suspension. It should be noted that the solvent is incapable of dissolving the amino acid, but does dissolve the TCF.

The chemistry of the process of the present invention using TCF for the preparation of ANCA has not yet been completely clarified. However, because of considerable differences in the mode of reaction between the use of TCF and the use of phosgene, it can reasonably be presumed that TCF is not decomposed into two mols of phosgene which then react with amino acids or salts thereof. But TCF reacts directly with the amino acids or salts thereof, as explained hereinafter.

It is believed that in the case where acid salts of amino acids are used the reaction readily occurs as shown in (A) below. Alternatively, in the case where free amino acids, ammonium or metallic salts of amino acids are used the reaction readily proceeds as shown in (B) below. As shown below the resultants (A1,) and (B1,) are cyclized into (C) 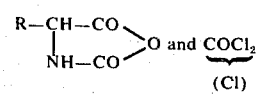

(C1)

(A) 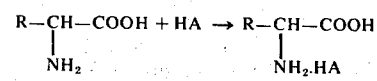

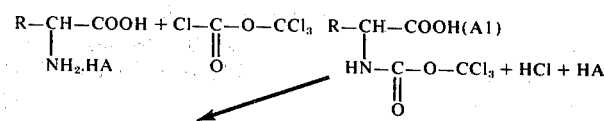

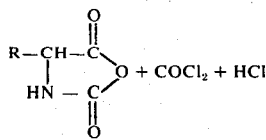

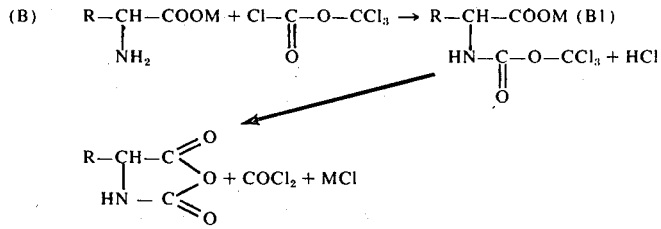

wherein R represents an amino acid residue, and M represents hydrogen, ammonium or metal.

For the purpose of better understanding, monovalent acids and metals are illustrated in the above schemes, but in the cases of di- or higher valent acid and metals the reaction schemes are the same as above illustrated.

It has been confirmed that the NCA-forming reaction according to the present invention goes to completion in a very short period of time with a high yield. It is considered that the reaction is mainly assisted by the evolution of the by-product phosgene (CI) and the TCF dissolved in the reaction system. The amount of the by-product phosgene is relatively small so that it is easy to collect the waste phosgene by using a suitable collecting device without deleterious influence upon human health. The reaction according to the present invention is preferably carried out at a temperature within the range of from an ambient temperature to 150°C for about 2 minutes to 6 hours.

Because TCF is a liquid having a boiling point of 127°–128°C and is readily soluble in various organic solvents, it is possible to carry out the reaction by using TCF in the liquid form. When TCF escapes as vapor from the reaction system, it can easily be recovered and recycled to the reaction system, e.g., by using a condenser. It is therefore sufficient to use TCF in about a mol equivalent to the amount of amino acid or its salt used as starting material. The reaction easily proceeds with a high speed.

As the amino acids may be used for the purpose of the present invention, it is possible to use any amino acids and derivatives thereof used for NCA-forming reactions of the known types as exemplified by neutral amino acids such as glycine, alanine, leucine, isoleucine, valine, proline, phenylalanine, cysteine, o-tert-butylserine, o-tert-butylthreonine, o-benzylserine, o-benzylthreonine, o-benzyltyrosine, S-benzylcysteine, etc.; ω-alkyl or ω-aralkyl derivatives of acidic amino acids such as β-alkylesters of aspartic acid [methyl, ethyl, propyl and isomers thereof, etc., as the alkyl group], γ-alkylesters of glutamic acid [methyl, ethyl, propyl and isomers thereof, butyl and its isomers, etc., as the alkyl group], γ-benzylesters of glutamic acid, etc.; N-substituted derivatives of basic amino acids such as Nε-acetyllysine, Nε-carbobenzoxylysine, Nδ-carbobenzoxyornithine, etc.; arginine; cystine; methionine, etc. All of these may be either optically active or inactive.

Examples of the salts of amino acids which may be used for the present invention include acid addition salts (for example, hydrochloride, sulfate, nitrate, phosphate, etc.) of amino acids or derivatives thereof which are capable of forming ANCA by reacting with phosgene (such as neutral amino acids, acidic amino acid monoester, N-derivatives of basic amino acids); ammonium salts and metallic salts (such as salts of alkali metals, e.g., sodium, potassium, etc.; salts of alkali earth metals, e.g., magnesium, etc.; as well as salts of metals which form salts with amino acids or derivatives thereof, e.g., aluminum, zinc, copper, silver, iron, nickel, mercury, etc.).

For the purpose of the present invention, it is possible to use various organic solvents such as hydrocarbons, halogenates, nitro-compounds, nitriles, esters, ketones, ethers, etc. (preferably those having carbon atoms of 1–8), which are used for the preparation of ANCA in the prior amino acid and phosgene reactions. Preferably examples of the solvents include: benzene, toluene, xylene (including its isomers), dichloromethane, chloroform, carbon tetrachloride, 1,2-dichloroethane, 1,2-dichloropropane, 1,1,1-trichloroethane, tetrachloroethane, trichloroethylene, perchloroethylene, chlorobenzene, dichlorobenzene (including its isomers), chlorotoluene (including its isomers), benzylchloride, fluorobenzene, fluorotoluene (including its isomers), nitrobenzene, nitrotoluene (including its isomers), methylacetate, ethylacetate, propylacetate (including its isomers), butylacetate (including its isomers), methylformate, ethylformate, propylformate (including its isomers), butylformate (including its isomers), acetonitrile, propionitrile, tetrahydrofuran, 1,4-dioxane, propylether (including its isomers), α-chloroethylether, ethyleneglycoldiethylether, methylethylketone, methylisobutylketone, etc.

However, if a mixture of an ether or ester with various other organic solvents is used as the reaction solvent, the reaction of converting amino acids or salts thereof into their respective NCAs can advantageously be accelerated (even a small amount of ethers or esters is very effective). Examples of preferable mixtures include mixtures of dioxane with 1,2-dichloroethane (hereinafter referred to as EDC), dioxane with methylenechloride, dioxane with chloroform, EDC with ethylacetate, EDC with tetrahydrofuran (hereinafter referred to as THF), benzene, toluene with THF, and chloroform with ethylacetate.

It has also been confirmed that when the TCF used for the reaction with the amino acid is still present in the reaction mixture after completion of the reaction, chlorine remains in the NCA produced, resulting in deleterious influence upon the quality of the final product. Therefore, as stated hereinafter, when chlorine reducing agent is not used, the use of TCF in excess amounts should be avoided.

ANCA having a lower chlorine content is frequently required. For example, the preparation of high grade polyglutamic acids requires ANCAs of γ-methyl-L-glutamate or γ-benzyl-L-glutamate having high purity and containing very low amounts of chlorine [e.g. J.A.C.S., Vol. 76, page 4492 (1954)]. In order to minimize the chlorine content in ANCA, there have conventionally been proposed some processes, such as, for example, repeated recrystallizations; purification by the addition of substituted amides, contacting the ANCA solution with silver oxide (Japanese Patent Publication No. 15939/1967), etc. However, these processes have the disadvantages of complicated operation and low yield and can hardly be applied with advantage to industrial processes.

According to another aspect of the present invention, it is possible to eliminate the chlorine content in the reaction mixture by adding thereto a suitable amount of carbon, aluminum oxide and/or basic aluminum chloride just before or immediately after the completion of the reaction. When carbon, etc. is added to the reaction mixture before completion of the reaction, the required amount of TCF may more or less increase because of the consumption by carbon, etc. It is advantageous to add carbon, etc., to the reaction system just before or immediately after completion of the reaction. It is possible to use carbon, etc. in an amount of 0.1–50% (preferably 0.5–20%) by weight of the amino acid or salts thereof used as starting material, though the amount used may vary with various conditions.

Before adding carbon, etc., the temperature of the reaction system is preferably reduced by 10°–50°C to prevent a possible bumping. The addition of carbon, etc. is preferably effected with agitation at a suitable temperature (e.g., at a temperature which is not lower than the reaction temperature) for from several minutes to several hours, if desired, with simultaneous charging of an inert gas such as nitrogen, carbon dioxide, etc. Contacting the reaction mixture with carbon, aluminum oxide and/or basic aluminum chloride is then discontinued by a suitable method (e.g. centrifugation, filtration under pressure, etc.) at a temperature sufficiently high to prevent the crystallization of ANCA.

The carbon, aluminum oxide and basic oxide may be used, for example, in the form of powder, grain or bar. For carbon, it is possible to use as graphite, coke, charcoal, coal, etc. Basic aluminum chloride may be represented by the formula:-

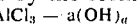

$$AlCl_3 - a(OH)_a$$

wherein $a$ is a number of from 2.99 to 0.01.

Subsequently, the reaction mixture is cooled, if desired, after concentration in vacuo, and the ANCA is recovered by crystallization. The ANCA thus obtained contains a very small amount of chlorine, and there is no need to recrystallize even when used for the preparation of polyamino acids without any after-treatment. The polyamino acids obtained have a high polymerization degree and a high purity.

The following non-limitative examples illustrate the invention.

EXAMPLE 1

In a 500 ml four-necked flask provided with a stirrer, a refluxing cooler, a thermometer and a dessicating calcium chloride tube, 15 g of γ-methyl-L-glutamate in the powder form (65 mesh in average) was suspended in 300 ml of EDC then heated to 60°–65°C. (Hereinafter γ-methyl-L-glutamate is referred to as MLG and the D-form is referred to as MDG). Immediately after the addition of 13.8 g of TCF to the mixture, the reaction commenced and an elevation of temperature by about 5°C was observed. When the reaction was further continued for about 40 min at 75°–80°C, the suspended MLG almost disappeared. After MLG was no longer visibly observed, the mixture was filtered, the filtrate was subjected to distillation under reduced pressure to remove the solvent. After cooling, the residue was mixed with about 40 ml of dried petroleum ether to effect the crystallization of ANCA. About 15 g of MLG-NCA was obtained. Melting point: 98°–99°C. Halogen content: 0.1%. The halogen content was determined by potentiometry according to JIS (Japanese Industrial Standard)— KO113. When recrystallized from about 60 ml of EDC, ANCA was obtained having a halogen content of 0.02%.

EXAMPLE 2

Various amino acids were converted into ANCA in a similar manner to that described in Example 1 except for changes of amino acid as raw material, reaction solvent, reaction temperature, temperature for the addition of TCF, amount of the added TCF, etc. In Tests 2, 3 and 7, the addition of petroleum ether was not performed. In Test 10, the size of the MDG used was 200 mesh and in Test 11, 30 mesh.

Control samples were prepared in a similar manner to that described above except that phosgen was used in place of TCF. In each test, phosgen was used in the same amount as TCF. The results obtained are shown in Table 1, from which it is apparent that the use of TCF gives ANCA with a higher yield.

Table 1

| Test | A | B | C | D | E | F | Control |
|------|---|---|---|---|---|---|---------|
| 1 | L-leucine 13.1g | dioxane 262ml | 19.8g 80°C | 90–100°C | 15min | 63% | 42% |
| 2 | ε-carbobenzoxy-L-lysine 14g | dioxane 210ml | 10.9g 80°C | 90–100°C | 30min | 66% | 44% |
| 3 | MDG 15g | dioxane 240ml | 23.0g 40°C | 75–80°C | 40min | 68% | 41% |
| 4 | MLG 15g | THF 320ml | 20.8g 50°C | 60–65°C | 60min | 65% | 39% |
| 5 | MDG 15g | benzene 300ml | 14.1g 70°C | 70–80°C | 100min | 44% | 35% |
| 6 | γ-benzyl-L-glutamate 10 g | toluene 170ml | 7.5g 60°C | 90–100°C | 120min | 50% | 38% |
| 7 | MLG | chloroform | 21.8g | 60–62°C | 100min | 65% | 40% |

Table 1-continued

| Test | A | B | C | D | E | F | Control |
|------|---|---|---|---|---|---|---------|
| 8 | 20g MLG 20g | 300ml EDC 300ml | 60°C 21.8g 40°C | 80–82°C | 90min | 70% | 45% |
| 9 | β-benzyl-L-aspartate 20.9g | chloroform 200ml | 19.8g 60–62°C 50°C | 60–62°C | 100min | 60% | 41% |
| 10 | MDG 15g | dioxane 240ml | 23.0g 75–80°C 50°C | 75–80°C | 40min | 72% | 47% |
| 11 | MDG 15g | dioxane 240ml | 23.0g 75–80°C 40°C | 75–80°C | 50min | 67% | 40% |

A = amino acid; used amount
B = solvent; used amount
C = amount of TCF; temp. for addition
D = reaction temperature
E = reaction time
F = yield
Note: THF denotes tetrahydrofuran.

EXAMPLE 3

Various tests were carried out in a similar manner to that described in Example 1 with the exception that the solvents used included different mixed solvents. In each test, a control sample was prepared by using phosgene in place of TCF. The results obtained are shown in Table 2, from which it is apparent that the present invention using TCF provides ANCA having a lower chlorine content with a higher yield.

EXAMPLE 4

The tests described in Example 3 were repeated by adding to the reaction mixture carbon, aluminum oxide or basic aluminum chloride during the reaction or first after the completion of the reaction to give ANCA. The chlorine content of the ANCA obtained are shown in Table 3 where each of the test numbers corresponds to that shown in Table 2 in Example 3.

Table 2

| Test | A | B | C | D | E | F |
|------|---|---|---|---|---|---|
| 1 | MLG | Chloroform | 100–110 | 60–62 | 75–80 | 0.02–0.05 |
| Con. | | | | | 50–55 | 0.04–0.15 |
| 2 | MDG | EDC | 90–110 | 75–81 | 75–80 | 0.02–0.05 |
| Con. | | | | | 50 | 0.05–0.15 |
| 3 | MLG | EDC:dioxane (10:1) | 30–40 | 80–83 | 80–85 | 0.02–0.03 |
| Con. | | | | | 60–65 | 0.05–0.15 |
| 4 | MLG | EDC:THF (10:1) | 30–40 | 80–82 | 80–85 | 0.02–0.03 |
| Con. | | | | | 60–65 | 0.05–0.10 |
| 5 | MDG | benzene:toluene:THF (10:5:1) | 60–80 | 80–85 | 80–90 | 0.02–0.03 |
| Con. | | | | | 55–70 | 0.05–0.15 |
| 6 | MLG | benzene:toluene:THF (10:5:1.5) | 40–60 | 80–85 | 80–95 | 0.02–0.03 |
| Con. | | | | | 60–75 | 0.05–0.15 |
| 7 | MLG | EDC:dioxane (15:1) | 30–40 | 80–85 | 80–90 | 0.02–0.025 |
| Con. | | | | | 60–70 | 0.05–0.10 |
| 8 | MLG | methylenechloride:dioxane (15:1) | 60–80 | 40–50 | 80–90 | 0.02–0.025 |
| Con. | | | | | 60–70 | 0.05–0.10 |
| 9 | MDG | chloroform:dioxane (15:1) | 50–60 | 60–65 | 80–95 | 0.03–0.04 |
| Con. | | | | | 60–65 | 0.10–0.15 |
| 10 | MLG | dioxane | 30–40 | 80–90 | 60–70 | 0.05–0.08 |
| Con. | | | | | 45–55 | 0.15–0.20 |
| 11 | MLG | THF | 40–50 | 62–66 | 60–70 | 0.06–0.09 |
| Con. | | | | | 45–50 | 0.15–0.25 |
| 12 | MLG | toluene | 180 | 80–85 | 44–55 | 0.15–0.20 |
| Con. | | | | | 30–35 | 0.20–0.30 |
| 13 | MLG | benzene | 100–130 | 80–81 | 40–80 | 0.10–0.15 |
| Con. | | | | | 20–40 | 0.20–0.35 |
| 14 | MLG | EDC:ethylacetate (15:1) | 50–70 | 75–80 | 80–95 | 0.02–0.03 |
| Con. | | | | | 60–75 | 0.05–0.15 |
| 15 | MLG | chloroform:ethylacetate (10:1) | 50–70 | 45–61 | 80–90 | 0.02–0.03 |
| Con. | | | | | 60–75 | 0.05–0.15 |
| 16 | MLG | EDC:ethylacetate (7:3) | 50–70 | 75–80 | 80–90 | 0.02–0.03 |
| Con. | | | | | 65–75 | 0.05–0.10 |

A = amino acid
B = reaction solvent
C = reaction time (min)
D = reaction temperature (°C)
E = yield
F = chlorine content (%)
Con. = Control Table 3

A = material for contacting and its amount
B = treating method
C = chlorine content in obtained ANCA

| Test | A | B | C |
|---|---|---|---|
| 1 | active carbon 3 g | Added after the completion of reaction. The reaction mixture was agitated at 60°C for 30 min with simultaneous charging of nitrogen gas. The carbon removed by filtration. | 0.01–0.015% |
| 2 | aluminum oxide 5 g | Added after the completion of reaction. Treated at 81°C for 15 min with simultaneous charging of nitrogen gas. | 0.01–0.015% |
| 3 | granulated carbon 5 g | Added at 20 min after the starting of reaction, and the reaction further continued. After the completion of the reaction the mixture was cooled to 60°C and nitrogen gas was charged for 10 min. | 0.005–0.01% |
| 4 | granulated carbon 3 g | Added at 20 min after the starting of reaction. The reaction was continued for further 30 min. After this, nitrogen gas was charged at 80°C for 10 min. | 0.008–0.01% |
| 5 | granulated carbon 10 g | Added after the completion of reaction. The reaction mixture was treated at 80°C for 15 min with simultaneous charging of carbon dioxide gas. | 0.005–0.01% |
| 6 | aluminum oxide 1 g | Added by suspending in 20 ml of EDC after the completion of reaction. The reaction mixture was treated at 80°C for 30 min with simultaneous charging of $CO_2$ gas. | 0.005–0.01% |
| 7 | granulated carbon column | After the completion of reaction, the reaction mixture was cooled to 60°C and charged together with $CO_2$ gas into a column packed with 100 ml of grained carbon under pressure. | 0.004–0.008% |
| 8 | graphite stick | After the completion of reaction, a graphite stick was put into the reaction Mixture, and the reaction was continued with agitation at 80°C for 1 hour. | 0.005–0.01% |
| 9 | active carbon 0.5 g | Added at 20 min after the starting of reaction, and the reaction was further contained for 30 min. After this, nitrogen gas was charged for 10 min. | 0.005–0.01% |
| 10 | aluminum oxide 5 g | Added at 20 min after the starting of reaction. The reaction was further continued for 30 min with simultaneous charging of nitrogen gas. | 0.02–0.03% |
| 11 | aluminum oxide 5 g | Same treatment as that described in Test 10. | 0.02–0.03% |
| 12 | granulated coke 3 g | Added at 2 hours after the starting of reaction. The reaction was further continued for 1 hour and then nitrogen gas was charged for 10 min. | 0.05–0.1% |
| 13 | coke 3 g | Same treatment as that described in Test 12. | 0.05–0.10% |
| 14 | active carbon (granulated) | Same treatment as that described in Test 9. | 0.005–0.01% |

Table 3-continued

A = material for contacting and its amount
B = treating method
C = chlorine content in obtained ANCA

| Test | A | B | C |
|------|---|---|---|
| 15 | active carbon (granulated) 3 g | Same treatment as that described in Test 3. | 0.005–0.01% |
| | 0.5 g | | |
| 16 | active carbon 0.5 g | Same treatment as that described in Test 14. | 0.005–0.01% |
| 14' | aluminum chloride 3 g | Same treatment as that described in Test 4. | 0.005–0.01% |
| | 3 g | | |
| 15' | carbon stick | Same treatment as that described in Test 8 | 0.005–0.01% |
| 3' | basic aluminum chloride 5 g | Same treatment as that described in Test 1. | 0.005–0.01% |

As apparent from the above, the chlorine content is reduced considerably when compared with those in Example 3. Each of the ANCA shown in Table 3 of Example 4 was synthesized in a similar manner to that described in Example 1. After the reaction, the reaction mixture was subjected to the above treatment, and if desired, the additive was removed therefrom by filtration. Subsequently, the solvent was distilled off from the reaction solution under reduced pressure to obtain crystals.

EXAMPLE 5

ANCA were chosen from among those obtained in Examples 1 and 2 and were subjected to polymerization at 20°C by using dioxane, 1,2-dichloroethane or a mixture thereof as a solvent and triethylamine as a polymerization initiator to prepare polyamide acids. The results obtained are shown in Table 4.

Table 4

A = ANCA used
B = solvent
C = concentration of polymer
D = ratio of initiator
E = state of polymer solution
F = reduced viscosity of polymer

| Test | A | B | C | D | E | F |
|------|---|---|---|---|---|---|
| 1 | synthesized in Example 1 | EDC:dioxane (9:1) | 10% | 30 | slightly turbid | 1.8 |
| 2 | synthesized in Test 1 of Example 2 | EDC:dioxane (9:1) | 8% | 50 | slightly turbid | 1.5 |
| 3 | synthesized in Test 2 of Example 2 | dioxane | 10% | 30 | slightly turbid | 1.4 |
| 4 | synthesized in Test 3 of Example 2 | EDC | 10% | 50 | almost transparent | 2.1 |

Note: Ratio of initiator was calculated by ANCA/triethylamine in mol. Reduced viscosity was determined at 20°C by using a dichloroacetic acid solution of the obtained polymer [concentration 0.4% (g/volume)]. A modified Oswald-type was used.

EXAMPLE 6

The ANCA obtained in Examples 3 and 4 were subject to the polymerization in a similar manner to that described in Example 5 under the following conditions. The state of the polymer solution and the degree of polymerization (reduced viscosity of polymer) are shown in Table 5.

Polymerization conditions:
solvent: EDC  initiator: triethylamine
concentration of polymer: 10%  temperature: 20°C
ratio of initiator: 50 (calculated by ANCA/triethylamine in mol)

Table 5

| Test | Used ANCA | State of solution | R-V* |
|------|-----------|-------------------|------|
| 1 | Test 1 of Example 3 | almost transparent | 2.3 |
| 2 | Test 1 of Example 4 | perfectly transparent | 3.1 |
| 3 | Test 3 of Example 3 | almost transparent | 2.6 |
| 4 | Test 3 of Example 4 | perfectly transparent | 3.8 |
| 5 | Test 7 of Example 3 | almost transparent | 2.1 |
| 6 | Test 7 of Example 4 | perfectly transparent | 2.9 |
| 7 | Test 14 of Example 3 | almost transparent | 2.4 |
| 8 | Test 14 of Example 4 | perfectly transparent | 3.0 |

Note: R-V* = reduced viscosity

As apparent from the comparison of Table 4 with Table 5, the polymer solutions obtained from the ANCA of Example 4 are superior in both the transparency and the degree of polymerization from those obtained from the ANCA of Example 3. Moreover, the former solutions were also superior in filtering property than the latter solutions.

EXAMPLE 7

Various salts of amino acids were converted into ANCA in a similar manner to that described in Example 1 with the exception of changes in the reaction solvent, temperature for addition of TCF, added amount of TCF, etc. The results obtained are shown in Table 6.

The ANCA is Test 1 which was crystallized by adding petroleum ether in a similar manner to that described in Example 1 had a melting point of 98°–99°C and a halogen content of 0.1%. The ANCA was recrystallized by using about 60 ml of EDC to give ANCA containing 0.02% of halogen.

In Tests 2 through 7, a control sample was prepared in a similar manner to that described above except that phosgene was used in place of TCF. Table 6 clearly shows that the present invention using TCF produces ANCA with a higher yield when compared with the conventional process using phosgene.

EXAMPLE 8

Similar treatments to that described in Example 1 were carried out respectively by using single solvents and mixed solvents as well as the salts of amino acids as substituents for the amino acids as starting materials. The tests were also carried out against the control samples which were prepared in a similar manner to that described above except that phosgene was used in place of TCF. The results obtained are shown in Table 7, from which it is apparent that the present invention using TCF provides ANCA having a lower chlorine content with a higher yield.

Table 7

| Test | Salts of amino acid | Reaction Solvent | Reaction time (min.) | Reaction temp. (°C) | yield (%) | Chlorine content (%) |
|---|---|---|---|---|---|---|
| 1 | MLG.HCl | ethylacetate | 50–60 | 78 | 60–70 | 0.05–0.09 |
| Con. |  |  |  |  | 35 | 0.10–0.15 |
| 2 | MLG.HCl | EDC:ethylacetate (7:3) | 60–80 | 75–80 | 80–90 | 0.02–0.03 |
| Con. |  |  |  |  | 30–35 | 0.05–0.055 |
| 3 | MDG.HCl | EDC | 90–110 | 75–82 | 70–75 | 0.02–0.05 |
| Con. |  |  |  |  | 55–60 | 0.065–0.070 |
| 4 | MDG.HCl | EDC:dioxane (10:1) | 30–90 | 75–82 | 70–80 | 0.01–0.02 |
| Con. |  |  |  |  | 45–50 | 0.03–0.04 |
| 5 | MlG.Ca salt | EDC | 150–180 | 82–83 | 70–75 | 0.02–0.05 |
| Con. |  |  |  |  | 60 | 0.08–0.09 |
| 6 | MLG.Ca salt | methylenechloride:dioxane (10:1) | 60–80 | 40–50 | 70–80 | 0.01–0.02 |
| Con. |  |  |  |  | 50–55 | 0.05–0.07 |
| 7 | leucine.Na salt | dioxane | 30–60 | 50–60 | 70–75 | 0.03–0.05 |
| Con. |  |  |  |  | 50–55 | 0.08–0.09 |
| 8 | leucine.Na salt | methylenechloride:dioxane (7:3) | 60–90 | 50–65 | 70–80 | 0.01–0.02 |
| Con. |  |  |  |  | 55–60 | 0.055–0.060 |
| 9 | alanine.Mg salt | THF | 80–100 | 50–60 | 60–65 | 0.03–0.05 |
| Con. |  |  |  |  | 45–50 | 0.080–0.085 |
| 10 | alanine.Mg salt | chloroform:THF (10:1) | 90–110 | 55–62 | 65–75 | 0.02–0.03 |
| Con. |  |  |  |  | 40–45 | 0.070–0.075 |

EXAMPLE 9

The products obtained from the tests of Example 8 were respectively treated with carbon and aluminum oxide to obtain samples of ANCA. The properties with respect to the chlorine content of the ANCA obtained are compared with each other in Table 8 where the test Table 6

A = salts of amino acids; amount used
B = solvent; amount used
C = TCF; amount; Temp. upon addition
D = reaction temperature
E = reaction time
F = yield
Control = yield
  amount of phosgene

| Test | A | B | C | D | E | F | Control |
|---|---|---|---|---|---|---|---|
| 1 | MLG.HCl 18.4 g | EDC 240 ml | 23.0 g 80°C | 80–82°C | 100 min. | 70% | — |
| 2 | L-serine silver salt 21.2 g | dioxane 250 ml | 19.8 g 30° | 30–50°C | 180 min. | 50% | 35% 20.3 g |
| 3 | L-threonine silver salt 9.5 g | dioxane 100 ml | 8.5 g 30°C | 30–50°C | 170 min. | 63% | 50% 9.2 g |
| 4 | β-benzyl-L-aspartate.HCl 15 g | EDC 250 ml | 23.0 g 50°C | 75–80°C | 120 min. | 60% | 35% 23.3 g |
| 5 | Leucine sodium salt 10 g | dioxane 150 ml | 13.0 g 50°C | 55°C | 60 min. | 65% | 45% 14.1 g |
| 6 | γ-benzyl-L-glutamate calcium salt 10 g | ethylacetate 200 ml | 7.5 g 60°C | 77°C | 90 min. | 65% | 40% 8.5 g |
| 7 | MLG sodium salt 15 g | THF 300 ml | 19 g 50°C | 66°C | 60 min. | 60% | 35% 20.1 g | numbers correspond to those shown in Table 7 of Example 8.

Table 8

A = material for contacting and its amount
B = treating method
C = chlorine content of ANCA obtained (%)

| Test | A | B | C |
|------|---|---|---|
| 1 | active carbon 0.5 g | Added to the reaction mixture after the completion of reaction. The reaction mixture was agitated at 60°C for 30 min with simultaneous charging of nitrogen gas. The carbon was removed by filtration. | 0.02–0.03 |
| 2 | active carbon 0.5 g | Similar treatment as that described in Test 1. | 0.005–0.01 |
| 3 | aluminum oxide 1 g | Added by suspending in 20 ml of EDC after the completion of reaction. The reaction mixture was treated at 80°C for 30 min with simultaneous charging of $CO_2$ gas. | 0.01–0.015 |
| 4 | aluminum oxide 1 g | Similar treatment as that described in Test 3. | 0.005–0.01 |
| 5 | graphite stick | After the completion of reaction, a graphite stick was put into the reaction mixture, and the reaction was continued with agitation at 80°C for 1 hour. | 0.01–0.015 |
| 6 | graphite stick | Similar treatment as that described in Test 5. | 0.005–0.01 |
| 7 | active carbon 3 g | Similar treatment as that described in Test 1. | 0.01–0.015 |
| 8 | active carbon 3 g | Similar treatment as that described in Test 1. | 0.005–0.01 |
| 9 | granulated carbon 5 g | Similar treatment as that described in Test 1. | 0.01–0.013 |
| 10 | granulated carbon 5 g | Similar treatment as that described in Test 1. | 0.005–0.01 |

As shown above, the chlorine content in each test decreases when compared with that in Example 8. All ANCA shown in Table 8 of Example 9 were synthesized in a similar manner to that described in Example 1. After the completion of the reaction each reaction product was subjected to the above treatment and the additive was, if desired, removed by filtration. Subsequently, the solvent was distilled off under reduced pressure to obtain crystals which were collected by filtration.

EXAMPLE 10

The ANCA obtained in Test 1 of Example 7 was subjected to polymerization at 20°C by using 1,2-dichloroethane or a mixture of dioxane and 1,2-dichloroethane as solvents and triethylamine as the polymerization initiator. The results of polyamide acids thus-obtained are shown in Table 9.

Table 9

A = concentration of polymer
B = ratio of initiator
C = state of polymer solution
D = reduced viscosity of polymer

| Test | ANCA Used | Solvent | A | B | C | D |
|------|-----------|---------|---|---|---|---|
| 1 | Synthesized in Test 1 of Example 7 | EDC:dioxane (9:1) | 10% | 30 | slightly turbid | 1.7 |
| 2 | Synthesized in Test 1 of Example 7 | EDC | 10% | 50 | almost transparent | 2.0 |

Note: Ratio of initiator was calculated by ANCA/triethylamine in mol. Reduced viscosity was determined in a similar manner to that described in Example 5. A modified Oswald-type was used.

EXAMPLE 11

The ANCA obtained in Examples 8 and 9 were subjected to polymerization under similar conditions to those described in Example 10. The state of polymer solution and the degree of polymerization (reduced viscosity of polymer) are shown in Table 10.

Polymerization conditions:
Solvent: EDC
Concentration of polymer: 10%
Ratio of initiator: 50
Initiator: triethylamine
Temperature: 20°C Table 10

| Test | ANCA Used | State of solution | Reduced viscosity |
|------|-----------|-------------------|-------------------|
| 1 | Test 1 of Example 8 | almost transparent | 2.2 |
| 2 | Test 1 of Example 9 | perfectly transparent | 3.0 |
| 3 | Test 3 of Example 8 | almost transparent | 2.7 |
| 4 | Test 3 of Example 9 | perfectly transparent | 3.9 |
| 5 | Test 5 of Example 8 | almost transparent | 2.0 |
| 6 | Test 5 of Example 9 | perfectly transparent | 3.0 |

As apparent from the comparison of Table 9 with Table 10, the polymer solutions obtained from ANCA of Example 9 are superior with respect to the transparency and the degree of polymerization to those of Example 8. Moreover, the former solutions are also superior in filtering property to the latter solutions.

What is claimed is:

1. A process for preparing N-carboxylic anhydrides of amino acids comprising the step of reacting an amino acid selected from the group consisting of glycine, alanine, leucine, isoleucine, valine, proline, phenylalanine, cysteine, O-tert-butylserine, O-tert-butylthreonine, O-benzylserine, O-benzylthreonine, O-benzyltyrosine, S-benzylcysteine, methyl aspartate, ethyl asparate, propyl aspartate, methyl glutamate, ethyl glutamate, propyl glutamate, butyl glutamate, benzyl glutamate, N-acetyllysine, N-carbobenzoxylysine, N-carbobenzoxyornithine, arginine, cystine, methionine, and salts thereof; with trichloromethylchloroformate in an amount of from about 0.75 to 2.1 moles per mol of the amino acid at a temperature of from 30° to 150°C in an organic solvent selected from the group consisting of benzene, toluene, xylene, dichloromethane, 1,2-dichloropropane, 1,1,1-trichloroethane, tetrachloroethane, trichloroethylene, perchloroethylene, chlorobenzene, dichlorobenzene, chlorotoluene, benzylchloride, fluorobenzene, fluorotoluene, nitrobenzene, nitrotoluene, methyl acetate, ethyl acetate, propyl acetate, butyl acetate, methyl formate, ethyl formate, propyl formate, butyl formate, acetonitrile, propionitrile, tetrahydrofuran, 1,4-dioxane, propyl ether, chloroethyl ether, ethyleneglycol diethyl ether, methyl ethyl ketone, methyl isobutyl ketone, mixtures of dioxane with 1,2-dichloroethane, dioxane with methylenechloride, dioxane with chloroform, 1,2-dichloroethane with ethylacetate, 1,2-dichloroethane with tetrahydrofuran, chloroform with ethylacetate, benzene with tetrahydrofuran, and toluene with tetrahydrofuran.

2. The process of claim 1 wherein said amino acid salt is a salt selected from the group consisting of hydrochlorides, sulfates, nitrates, phosphates, sodium salts, potassium salts, magnesium salts, aluminum salts, zinc salts, copper salts, silver salts, iron salts, nickel salts and mercury salts.

3. The process of claim 1 wherein the reaction mixture is contacted, just before or immediately after completion of the reaction, with a chlorine reducing agent selected from the group consisting of carbon, basic aluminum chloride and aluminum oxide.

4. The process of claim 3 wherein the reaction mixture is contacted with the chlorine reducing agent immediately after completion of the reaction.

5. The process of claim 3 wherein the chlorine reducing agent is used in an amount of about 0.1 – 50% by weight based on the amino acid.

* * * * *